United States Patent
Kang et al.

(10) Patent No.: US 9,207,062 B2
(45) Date of Patent: Dec. 8, 2015

(54) DISTORTION CORRECTED OPTICAL COHERENCE TOMOGRAPHY SYSTEM

(71) Applicant: The Johns Hopkins University, Baltimore, MD (US)

(72) Inventors: Jin U. Kang, Ellicott City, MD (US); Xuan Liu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 129 days.

(21) Appl. No.: 13/709,885

(22) Filed: Dec. 10, 2012

(65) Prior Publication Data

US 2014/0160484 A1 Jun. 12, 2014

(51) Int. Cl.
*G01B 9/02* (2006.01)
*A61B 5/00* (2006.01)

(52) U.S. Cl.
CPC .......... *G01B 9/02045* (2013.01); *A61B 5/0066* (2013.01); *A61B 5/0073* (2013.01); *G01B 9/0207* (2013.01); *G01B 9/02077* (2013.01); *G01B 9/02091* (2013.01)

(58) Field of Classification Search
CPC ........... G01B 9/02076; G01B 9/02091; G01B 9/02044; G01B 9/02004; G01B 9/02083; G01B 9/02045; G01B 9/02077; G01B 11/0675; G01B 9/02061
USPC .......................... 356/479, 497, 511, 477, 456
See application file for complete search history.

(56) References Cited

U.S. PATENT DOCUMENTS

| | | | |
|---|---|---|---|
| 6,549,801 B1* | 4/2003 | Chen et al. ............ | 600/425 |
| 7,245,382 B2* | 7/2007 | Ronnekleiv ............ | 356/477 |
| 2003/0103212 A1* | 6/2003 | Westphal et al. ...... | 356/479 |
| 2004/0239943 A1* | 12/2004 | Izatt et al. ............ | 356/479 |
| 2009/0168017 A1* | 7/2009 | O'Hara et al. ........ | 351/205 |
| 2010/0245836 A1* | 9/2010 | Kulkarni et al. ...... | 356/479 |
| 2011/0170111 A1* | 7/2011 | Rolland et al. ........ | 356/479 |
| 2011/0267340 A1* | 11/2011 | Kraus et al. .......... | 345/419 |
| 2012/0320381 A1* | 12/2012 | Okada .................. | 356/484 |
| 2013/0188140 A1* | 7/2013 | Bagherinia et al. ... | 351/206 |

(Continued)

OTHER PUBLICATIONS

Ahmad et al., "Cross-correlation-based image acquisition technique for manually-scanned optical coherence tomography," Opt. Express 17(10), 8125-8136 (2009).

(Continued)

*Primary Examiner* — Tarifur Chowdhury
*Assistant Examiner* — Mohamed Amara
(74) *Attorney, Agent, or Firm* — Venable LLP; Henry J. Daley; Laura G. Remus

(57) ABSTRACT

An axial motion distortion-corrected optical coherence tomography system. The system can include an optical coherence tomography sensor, a light source, a fiber-optic system arranged to provide a reference beam and an observation beam, an optical detection system arranged to receive combined light from the reference beam and the observation beam and to provide detection signals, and a data processing system arranged to receive said detection signals, construct a plurality of A-scans from said detection signals, and construct one or more images from said plurality of A-scans. The data processing system can be configured to correct distortion in the images caused by net axial motion of at least one of said optical coherence tomography sensor or a target of said optical coherence tomography sensor by calculating an estimate of the net axial motion using Doppler shift, and then shifting the A-scans according to the estimate.

7 Claims, 1 Drawing Sheet

(56) References Cited

U.S. PATENT DOCUMENTS

| | | | |
|---|---|---|---|
| 2014/0078512 A1* | 3/2014 | Kang et al. | 356/497 |
| 2014/0152998 A1* | 6/2014 | Okuda | 356/498 |
| 2015/0009507 A1* | 1/2015 | Yasuno et al. | 356/479 |

OTHER PUBLICATIONS

Becker et al., "State estimation and feedforward tremor suppression for a handheld micromanipulator with a Kalman filter," IEEE/RSJ, International Conference on Intelligent Robots and Systems, 5160-6165(Sep. 25-30, 2011).

Boppart et al., "Forward-imaging instruments for optical coherence tomography," Opt. Lett. 22 (21), 1618-1620 (1997).

Boppart et al., "Optical coherence tomography: feasibility for basic research and image-guided surgery of breast cancer," Breast Cancer Res. Treatment 84(2), 85-97(2004).

Boppart et al., "Intraoperative assessment of microsurgery with three-dimensional optical coherence tomography," *Radiology*, vol. 208, pp. 81-86, 1998.

Chen et al., "Noninvasive imaging of in vivo blood flow velocity using optical Doppler tomography," Opt. Lett. 22(14), 1119-1121(1997).

Duncan et al., "Processing algorithms for tracking speckle shifts in optical elastography of biological tissues, " J. Biomed. Opt. 6(4), 418-426(2001).

Ha et al., "Compensation of motion artifacts in catheter-based optical frequency domain imaging," Opt. Express 18(11), 11418-11427 (May 2010).

Han et al., "Handheld forward-imaging needle endoscope for ophthalmic optical coherence tomography inspection," J. Biomed. Opt. 13(2), 020505(2008).

Huang et al., "Motion compensated fiber-optic confocal microscope based on a common-path optical coherence tomography distance sensor," Opt. Eng. 50(8), 083201 (Aug. 2011).

Huang et al., "Noncontact common-path Fourier domain optical coherence tomography method for in vitro intraocular lens power measurement", J. Biomed. Opt. 16(12), 126005(Dec. 2011).

Huang et al., "Optical coherence tomography," Science, 254(5035), 1178-1181(1991).

Huang et al., "Real-time 3D and 4D Fourier domain Doppler optical coherence tomography based on dual graphics processing units," Biomed. Opt. Express 3(9), 2162-2174 ( Aug. 2012).

Huber et al., "Buffered Fourier domain mode locking: unidirectional swept laser sources for optical coherence tomography imaging at 370,000 lines/s," Opt. Lett., vol. 31, pp. 2975-2977, 2006.

Huo et al., "Forward-viewing resonant fiber-optic scanning endoscope of appropriate scanning speed for 3D OCT imaging," Opt. Express 18(14),14375-14384(Jul. 2010).

Iftimia et al., "Adaptive ranging for optical coherence tomography," Opt. Express 12(17), 4025-4034 (2004).

Jafri et al., "Optical coherence tomography guided neurosurgical procedures in small rodents," J. Neurosci. Methods 176(2), 85-89 (2009).

Jung et al., "Three-dimensional optical coherence tomography employing a 2-axis microelectromechanical scanning mirror," IEEE J. Sel. Top. Quantum Electron. 11(4), 806-810(2005).

Kang et al., "Endoscopic functional Fourier domain common path optical coherence tomography for microsurgery," IEEE J. Sel. Top. Quantum Electron. 16(4), 781-792(Jul./Aug. 2010).

Kang et al., "Real-time three-dimensional Fourier-domain optical coherence tomography video image guided microsurgeries," J. Biomed. Opt. 17(8), 081403 (Aug. 2012).

Klein et al., "Megahertz OCT for ultrawide-field retinal imaging with a 1050nm Fourier domain mode-locked laser," Opt. Express, vol. 19, pp. 3044-3062, Feb. 2011.

Lee et al., "Motion correction for phase-resolved dynamic optical coherence tomography imaging of rodent cerebral cortex," Opt. Express 19(22), 21258-21270 (Oct. 2011).

Leitgeb et al., "Ultrahigh resolution Fourier domain optical coherence tomography," Opt. Express 12(10), 2156-2165(2004).

Liu et al., "Distortion-free freehand-scanning OCT implemented with real-time scanning speed variance correction," Opt. Express 20(15), 16567-16583 (Jul. 2012).

Maguluri et al., "Three dimensional tracking for volumetric spectral-domain optical coherence tomography," Opt. Express 15(25), 16808-16817 ( 2007).

Oh et al., ">400 kHz repetition rate wavelength-swept laser and application to high-speed optical frequency domain imaging," Opt. Lett., vol. 35, pp. 2919-2921,Sep. 2010.

Potsaid et al., "Ultrahigh speed 1050nm swept source / Fourier domain OCT retinal and anterior segment imaging at 100,000 to 400,000 axial scans per second," Opt. Express, vol. 18, pp. 20029-20048, Sep. 2010.

Potsaid et al., "Ultrahigh speed Spectral / Fourier domain OCT ophthalmic imaging at 70,000 to 312,500 axial scans per second," Opt. Express, vol. 16, pp. 15149-15169, 2008.

Singh et al., "Physiological tremor during retinal microsurgery," Proc. 28th Annual Conf. IEEE Eng. Med. Bio. Soc.,171-172(2002).

Song et al., "Active tremor cancellation by a "Smart" handheld vitreoretinal microsurgical tool using swept source optical coherence tomography," Opt. Express 20, 23414-23421 (Oct. 2012).

Tan et al., "In-fiber common-path optical coherence tomography using a conical-tip fiber," Opt. Express 17(4),2375-2380(2009).

Vakhtin et al., "Common-path interferometer for frequency-domain optical coherence tomography," App. Opt. 42(34), 6935-6958 (2003).

Wieser et al., "Multi-Megahertz OCT: High quality 3D imaging at 20 million A-scans and 4.5 GVoxels per second," Opt. Express, vol. 18, pp. 14685-14704, 2010.

Zhang et al., "A surface topology for microsurgery guidance and intervention based on common-path optical coherence tomography," IEEE Trans. on Biomed. Eng. 56(9),2318-2321(2009).

Zhang et al., "Common-path low-coherence interferometry fiber-optic sensor guided micro-incision," J. Biomed. Opt. 16(9),095003(Sep. 2011).

Zhang et al., "Real-time intraoperative 4D full-range FD-OCT based on the dual graphics processing units architecture for microsurgery guidance," Biomed. Opt. Express. 2(4), 764-770 (Apr. 2011).

Zysk et al., "Optical coherence tomography: a review of clinical development from bench to bedside," J. Biomed. Opt. 12(5), 051403 (2007).

\* cited by examiner

DISTORTION CORRECTED OPTICAL COHERENCE TOMOGRAPHY SYSTEM

FEDERAL FUNDING

This invention was made with Government support of Grant Nos. R01 EY021540 and BRP, 1R01 EB 007969-01, awarded by the Department of Health and Human Services, The National Institutes of Health (NIH). The U.S. Government has certain rights in this invention.

BACKGROUND

1. Field of Invention

The field of the currently claimed embodiments of this invention relates to optical coherence tomography systems, and more particularly to axial motion-compensated optical coherence tomography systems.

2. Discussion of Related Art

Optical coherence tomography (OCT) has been viewed as an "optical analogy" of ultrasound sonogram (US) imaging since its invention in early 1990's (D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical coherence tomography," Science, vol. 254, pp. 1178-1181, 1991). Compared to the conventional image-guided interventions (IGI) using modalities such as magnetic resonance imaging (MRI), X-ray computed tomography (CT) and ultrasound (US) (T. Peters and K. Cleary, Image-Guided Interventions: Technology and Applications, Springer, 2008), OCT has much higher spatial resolution and therefore possesses great potential for applications in a wide range of microsurgeries, such as vitreo-retinal surgery, neurological surgery and otolaryngologic surgery.

As early as the late 1990's, interventional OCT for surgical guidance using time domain OCT (TD-OCT) at a slow imaging speed of hundreds of A-scans/s has been demonstrated (S. A. Boppart, B. E. Bouma, C. Pitris, G. J. Tearney, J. F. Southern, M. E. Brezinski, J. G. Fujimoto, "Intraoperative assessment of microsurgery with three-dimensional optical coherence tomography," Radiology, vol. 208, pp. 81-86, 1998). Thanks to the technological breakthroughs in Fourier domain OCT (FD-OCT) during the last decade, ultrahigh-speed OCT is now available at >100,000 A-scan/s. For example, see the following:

B. Potsaid, I. Gorczynska, V. J. Srinivasan, Y. Chen, J. Jiang, A. Cable, and J. G. Fujimoto, "Ultrahigh speed Spectral/Fourier domain OCT ophthalmic imaging at 70,000 to 312,500 axial scans per second," Opt. Express, vol. 16, pp. 15149-15169, 2008.

R. Huber, D. C. Adler, and J. G. Fujimoto, "Buffered Fourier domain mode locking: unidirectional swept laser sources for optical coherence tomography imaging at 370,000 lines/s," Opt. Lett., vol. 31, pp. 2975-2977, 2006.

W-Y. Oh, B. J. Vakoc, M. Shishkov, G. J. Tearney, and B. E. Bouma, ">400 kHz repetition rate wavelength-swept laser and application to high-speed optical frequency domain imaging," Opt. Lett., vol. 35, pp. 2919-2921, 2010.

B. Potsaid, B. Baumann, D. Huang, S. Barry, A. E. Cable, J. S. Schuman, J. S. Duker, and J. G. Fujimoto, "Ultrahigh speed 1050nm swept source/Fourier domain OCT retinal and anterior segment imaging at 100,000 to 400,000 axial scans per second," Opt. Express, vol. 18, pp. 20029-20048, 2010.

W. Wieser, B. R. Biedermann, T. Klein, C. M. Eigenwillig, and R. Huber, "Multi-Megahertz OCT: High quality 3D imaging at 20 million A-scans and 4.5 GVoxels per second," Opt. Express, vol. 18, pp. 14685-14704, 2010.

T. Klein, W. Wieser, C. M. Eigenwillig, B. R. Biedermann, and R. Huber, "Megahertz OCT for ultrawide-field retinal imaging with a 1050 nm Fourier domain mode-locked laser," Opt. Express, vol. 19, pp. 3044-3062, 2011.

For a spectrometer-based SD-OCT, an ultrahigh speed CMOS or CCD line scan camera based system has achieved up to 312,500 line/s in 2008 (Potsaid et al.); while for a swept laser type OCT, >20,000,000 line/s rate was achieved by multi-channel FD-OCT using a Fourier Domain Mode Locking (FDML) laser in 2010 (Wieser et al.).

Fourier-domain optical coherence tomography (FD-OCT) is a high-speed high-resolution three-dimensional imaging modality widely used in biomedical imaging. For OCT to find applications in the interventional imaging area, real-time image processing and display are required.

Optical coherence tomography (OCT) is a non-invasive, high speed, high-resolution, three-dimensional imaging modality that is widely being used for biomedical application [1, 2]. The real-time non-invasive depth-resolved imaging of tissue structure and flow information provided by OCT can be highly valuable information that can assist physicians in making real-time decisions during surgical procedures such as neurosurgery, tumor resection, microvascular anastomosis, and retinal microsurgery [2-10].

In many circumstances, it is more convenient to use a simple hand-held, manually-scanned probe to obtain OCT images of tissues and organs which might otherwise be inaccessible using standard mechanical scanning heads [6]. A hand-held image probe has the following advantages. First, it is small and lightweight, making it easy to access tight spaces. Second, surgeons are intimately familiar with hand-held instruments which can leverage the surgeons' experience and skills with little training. Third, a small hand-held instrument offers greater safety because the surgeon can more easily override or remove the instrument in cases of malfunction [11]. Finally it offers the surgeon great freedom to obtain any image size, for example a larger field-of-view compared to views constrained by apertures of scanning lenses or other endoscopic probes [12-15].

A hand-held probe, however, poses additional challenges over mechanically-rigid scanners. First, non-uniform motion of the probe during lateral manual scanning will cause image distortion and inaccuracy. Earlier work by Ahmed et al. and more recent work by our lab provide solutions to correct non-uniform scanning speed artifact using decorrelation of adjacent A-lines [6, 16]. Second, physiological tremor composed of low and high frequency amplitudes over 100 μm [17] would cause large motion artifacts in acquired images. Third, involuntary motions of a subject may also cause OCT imaging artifacts. Finally, the manual scan across and close to the target surface is highly risky—especially involving fragile tissue. For example, in the context of retinal surgery, the retina is only ~350 μm for humans, and tearing them can permanently damage eyesight. Scanning while maintaining a larger distance between the probe tip and target surface is not an ideal solution since that degrades image quality and the imaging depth is typically limited to 3-5 millimeters. While motion is in the form of both axial and lateral directions, axial motion is the primary concern due to its direct effects on image quality. There have been methods used to compensate for the sample surface topology and axial motion in OCT to keep a good system sensitivity and image range, for example the adaptive ranging technique for time-domain OCT (TDOCT) [18] and the reference mirror tracking method for spectral domain OCT (SDOCT) [19]. Common path optical coherence tomography (CP-OCT) is a simple, all-fiber-based technique that shares reference and probe arm which circumvents group velocity dispersion and polarization compensation [20]. It has been widely investigated for various medical applications [21-24]. CP-OCT has also recently been demonstrated for its effectiveness, simplicity, and integrability for surface topology and motion compensation [25] and smart surgical tools [26]. There thus remains a need for improved optical coherence tomography systems that provide motion compensation.

SUMMARY

According to some embodiments of the present invention, a distortion-corrected optical coherence tomography system is disclosed. The system can include an optical coherence tomography sensor, a light source, a fiber-optic system arranged to provide a reference beam and an observation beam, an optical detection system arranged to receive combined light from the reference beam and the observation beam and to provide detection signals, and a data processing system arranged to receive said detection signals, construct a plurality of A-scans from said detection signals, and construct one or more images from said plurality of A-scans. The data processing system can be configured to correct distortion in the images caused by net axial motion of at least one of said optical coherence tomography sensor or a target of said optical coherence tomography sensor by calculating an estimate of the net axial motion using Doppler shift, and then shifting the A-scans axially according to the estimate.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

As discussed above, Optical coherence tomography (OCT) is a high resolution optical imaging modality with many medical applications. In some conventional OCT systems, a mechanical scanner can scan the beam according to a pre-defined scanning pattern to form two dimensional (2D) or three dimensional (3D) images. On the other hand, OCT scans can also be performed manually with a hand-held sensor that does not use a mechanical device to scan the beam. This type of hand-held sensors could be made very compact and light-weight. However, during free-hand scanning, the axial distance between sensor and sample surface varies due to the axial motion of human hands and causes image distortion.

Figure 1:
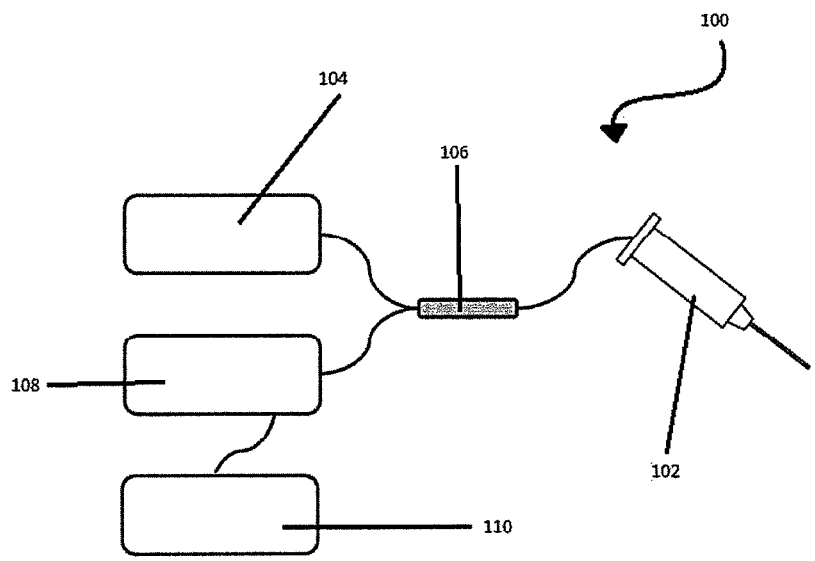
FIG. 1 is a schematic illustration of a distortion-corrected optical coherence tomography system according to an embodiment of the current invention.

FIG. 1 provides a schematic illustration of a distortion-corrected optical coherence tomography system 100 according to an embodiment of the current invention. Distortion-corrected optical coherence tomography system 100 can be any type of optical coherence tomography system as desired. In some embodiments, distortion-corrected optical coherence tomography system 100 can be a spatially encoded frequency domain OCT, a time encoded frequency domain OCT, a time domain OCT, or any other type of OCT as desired.

Distortion-corrected optical coherence tomography system 100 can include an optical coherence tomography sensor 102. Optical coherence tomography sensor can be a mechanical scanner, a handheld sensor or probe, or any other type of sensor as desired.

Distortion-corrected optical coherence tomography system 100 can include a light source 104. The terms "light" or "optical" as used herein are intended to have a broad meaning that can include both visible and non-visible regions of the electromagnetic spectrum. For example, visible, near infra-red, infrared and ultraviolet light are all considered as being within the broad definition of the term "light." Light source 104 can provide any type of light as desired. In some embodiments, light source 104 can be, for example, a superluminescent (SLED) light source.

Distortion-corrected optical coherence tomography system 100 can include a fiber optic system 106. Fiber optic system 106 can be optically coupled to light source 104 and said optical coherence tomography sensor 102, and can be arranged or otherwise configured to provide a reference beam and an observation beam. FIG. 1 shows an example of an embodiment in which the observation beam and the reference beam are provided along the same fiber optic path to optical coherence tomography sensor 102. In other embodiments, the observation beam and the reference beam can be provided along separate fiber optic paths within fiber optic system 106.

Distortion-corrected optical coherence tomography system 100 can also include optical detection system 108. Optical detection system 108 can be arranged or otherwise configured to receive combined light from the reference beam and observation beam of fiber optic system 106. Optical detection system 108 can also provide detection signals based on the combined light received from fiber optic system 106.

In some embodiments, the motion-compensated optical coherence tomography system 100 can further include a data processing system 110 configured to receive detection signals from optical detection system 108 and generate the any type of image, for example optical coherence tomography A-scans, images constructed from a plurality of optical coherence tomography A-scans, or any other type of image as desired. The data processing system 110 can be a workstation, for example. However, the broad concepts of the current invention are not limited to this example. Other data processing systems could be used according to the particular application. For example, the data processing system could be an application specific system, such as, but not limited to one or more ASICs and/or FPGAs. The data processing system could also be a personal computer, a laptop computer, a tablet computer, etc. It could also be a local or distributed computer, such as a computing system distributed over a local or wide area network, including the internet. The data processing system can also include one or more CPUs for running software and/or one or more graphics processing units (GPUs).

In some embodiments, the data processing system 110 can be further configured to perform distortion correction of the detection signals. For example, in some embodiments, data processing system 110 can construct an image using a plurality of A-scans. This image can be distorted by axial motion of the optical coherence tomography sensor, which causes shifts in the A-scans forming the image. Data processing system 110 can calculate an estimate of said axial motion using Doppler shift as described below, and then correct the distortion in the image by shifting the A-scans according to the calculated estimate.

Further additional concepts and embodiments of the current invention will be described by way of the following examples. However, the broad concepts of the current invention are not limited to these particular examples.

EXAMPLES

Figure 2A:
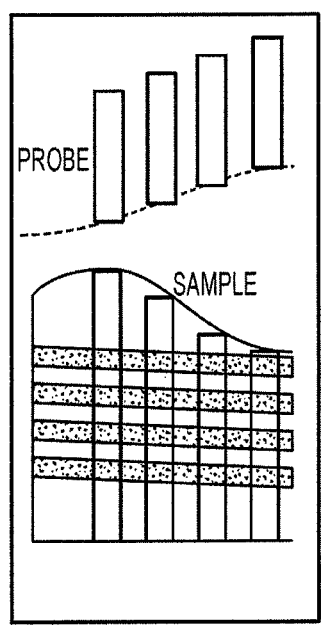
FIG. 2 shows (a) an OCT sensor experiencing axial motion scans across a sample, and (b) stacking sequentially obtained A-scans leading to an image with axial distortion.
Figure 2B:
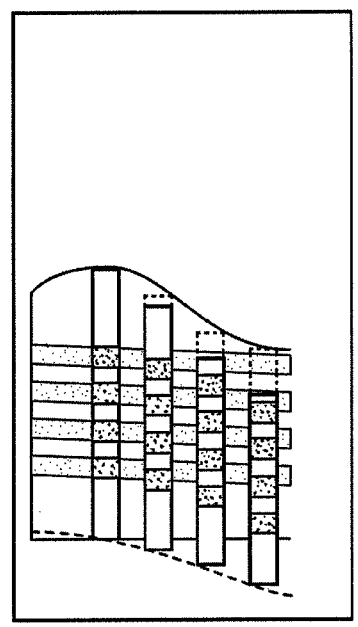

During free-hand scanning, the axial distance between sensor and sample surface varies randomly due to the axial motion of human hands and sample, and causes image distortion. If the sensor moves as shown in the right Figure during free hand scanning, simply stacking sequentially obtained Ascans will lead to an image with axial distortion as shown in FIG. 2B. In FIGS. 2A and 2B, the tilted stripes are used to represent sample structural feature; the dashed curve represents the trajectory of the axial hand motion; the solid curve represents the actual sample surface.

In this example, we describe a method that corrects axial motion distortion described in FIG. 2B, by using inter-Ascan global Doppler phase shift. Optical Doppler tomography (ODT) has been used in non-invasive blood flow measurement. In ODT, the phase difference of complex OCT signal between pixels in adjacent Ascans is used to quantify the speed of moving scatterers in axial direction. Alternatively, we can use Doppler frequency to estimate the axial motion of a hand-held sensor, assuming that the sample itself does not move. In reality both sensor and sample move, and the calculated phase shift will be due to the net motion. Thus, the method works even if there is a significant sample motion. Due to the motion of the sensor, all the pixels at different axial positions in an Ascan (denoted by $I_n$ in Eq (1)) experience the same phase shift as compared to the previous Ascan(denoted by $I_{n-1}$ in Eq (1)). Therefore, a global phase shift, $\Delta\phi$, can be calculated for Ascan by averaging the phase shift of all the pixels, as shown in Eq (1).

$$\Delta\varphi = \int \tan^{-1}\left[\frac{\mathrm{Im}[\tilde{I}_n(z) \bullet I_{n-1}^*(z)]}{\mathrm{Re}[\tilde{I}_n(z) \bullet I_{n-1}^*(z)]}\right] dz \quad (1)$$

With the global phase shift obtained, we are able to calculate the speed of axial motion using Eq (2) in which $\lambda_0$ indicates the central wavelength of light source used in OCT and $\Delta t$ indicates time interval between the Ascans used for the calculation of $\Delta\phi$.

$$v(t) = \frac{\lambda_0}{\Delta t}\left(\frac{\Delta\varphi}{4\pi}\right) \quad (2)$$

Subsequently, axial displacement d(t) due to axial motion can be obtained by taking the time integral of v(t), as shown in Eq (3). The distorted image can be then restored by shifting Ascans by d(t).

$$d(t) = \int_0^t v(t')dt' \quad (3)$$

REFERENCES AND LINKS

1. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, " Optical coherence tomography," Science, 254(5035), 1178-1181(1991).
2. B. E. Bouma, *Handbook of Optical Coherence Tomography*, (New York: Marcel Dekker, 2001).
3. A. M. Zysk, F. T. Nguyen, A. L. Oldenburg, D. L. Marks, and S. A. Boppart, "Optical coherence tomography: a review of clinical development from bench to bedside," J. Biomed. Opt. 12(5), 051403 (2007).
4. S. A. Boppart, W. Luo, D. L. Marks, and K. W. Singletary, "Optical coherence tomography: feasibility for basic research and image-guided surgery of breast cancer," Breast Cancer Res. Treatment 84(2), 85-97(2004).
5. M. S. Jafri, R. Tang, and C M. Tang, "Optical coherence tomography guided neurosurgical procedures in small rodents," J. Neurosci. Methods 176(2), 85-89 (2009).
6. A. Ahmad, S. G. Adie, E. J. Chaney, U. Sharma, and S. A. Boppart, "Cross-correlation-based image acquisition technique for manually-scanned optical coherence tomography," Opt. Express 17(10), 8125-8136 (2009).
7. K. Zhang and J. U. Kang, "Real-time intraoperative 4D full-range FD-OCT based on the dual graphics processing units architecture for microsurgery guidance," Biomed. Opt. Express. 2(4), 764-770 (2011).
8. J. U. Kang, Y. Huang, K. Zhang, Z. Ibrahim, J. Cha, W. P. A. Lee, G. Brandacher and P. L. Gehlbach, " Real-time three-dimensional Fourier-domain optical coherence tomography video image guided microsurgeries," J. Biomed. Opt. 17(8), 081403 (2012).
9. Z. P. Chen, T. E. Milner, S. Srinivas, X. Wang, A. Malekafzali, M. J. C. V. Gernert, and J. S. Nelson, "Noninvasive imaging of in vivo blood flow velocity using optical Doppler tomography," Opt. Lett. 22(14), 1119-1121 (1997).
10. Y. Huang, X. Liu, and J. U. Kang, " Real-time 3D and 4D Fourier domain Doppler optical coherence tomography based on dual graphics processing units," Biomed. Opt. Express 3(9), 2162-2174 (2012).
11. B. C. Becker, R. A. MacLachlan, and C. N. Riviere, "State estimation and feedforward tremor suppression for a handheld micromanipulator with a Kalman filter," IEEE/RSJ, International Conference on Intelligent Robots and Systems, 5160-6165(2011).
12. S. A. Boppart, B. E. Bouma, C. Pitris, G. J. Tearney, and J. G. Fujimoto, "Forward-imaging instruments for optical coherence tomography, " Opt. Lett. 22 (21), 1618-1620 (1997).
13. W. G. Jung, J. Zhang, L. Wang, P. Wilder-Smith, Z. P. Chen, D. T. McCormick, and N. C. Tien, "Three-dimensional optical coherence tomography employing a 2-axis microelectromechanical scanning mirror," IEEE J. Sel. Top. Quantum Electron. 11(4), 806-810(2005).
14. S. Han, M. V. Sarunic, J. Wu, M. Humayun, and C. H. Yang, "Handheld forward-imaging needle endoscope for ophthalmic optical coherence tomography inspection," J. Biomed. Opt. 13(2), 020505(2008).
15. L. Huo, J. Xi, Y. Wu, and X. Li, "Forward-viewing resonant fiber-optic scanning endoscope of appropriate scanning speed for 3D OCT imaging," Opt. Express 18(14),14375-14384(2010).

16. X. Liu, Y. Huang, and J. U. Kang, "Distortion-free freehand-scanning OCT implemented with real-time scanning speed variance correction," Opt. Express 20(15), 16567-16583 (2012).
17. S. P. N. Singh and C. N. Riviere, "Physiological tremor during retinal microsurgery," Proc. 28th Annual Conf. IEEE Eng. Med. Bio. Soc.,171-172(2002).
18. N. V. Iftimia, B. E. Bouma, J. F. de Boer, B. H. Park, B. Cense and G. J. Tearney, "Adaptive ranging for optical coherence tomography," Opt. Express 12(17), 4025-4034 (2004).
19. G. Maguluri, M. Mujat, B. H. Park, K. H. Kim, W. Sun, N. V. Iftimia, R. D. Ferguson, D. X. Hammer, T. C. Chen, and J. F. de Boer, "Three dimensional tracking for volumetric spectral-domain optical coherence tomography," Opt. Express 15(25), 16808-16817 (2007).
20. A. Vakhtin, D. Kane, W. Wood and K. Peterson, "Common-path interferometer for frequency-domain optical coherence tomography," App. Opt. 42(34), 6935-6958 (2003).
21. Y. Huang, K. Zhang, J. U. Kang, D. Calogero, R. H. James, I. Ilev, "Noncontact common-path Fourier domain optical coherence tomography method for in vitro intraocular lens power measurement", J. Biomed. Opt. 16(12), 126005(2011).
22. J. U. Kang, J. H. Han, X. Liu, K. Zhang, C. G. Song and P. Gehlbach, "Endoscopic functional Fourier domain common path optical coherence tomography for microsurgery," IEEE J. Sel. Top. Quantum Electron. 16(4), 781-792(2010).
23. Y. Huang, K. Zhang, C. Lin, and J. U. Kang, "Motion compensated fiber-optic confocal microscope based on a common-path optical coherence tomography distance sensor, " Opt. Eng. 50(8), 083201 (2011).
24. K. M. Tan, M. Mazilu, T. H. Chow, W. M. Lee, K. Taguchi, B. K. Ng, W. Sibbett, C. S. Herrington, C. T. A. Brown and K. Dholakia, "In-fiber common-path optical coherence tomography using a conical-tip fiber," Opt. Express 17(4),2375-2380(2009).
25. K. Zhang W. Wang, J. H. Han and J. U. Kang, "A surface topology for microsurgery guidance and intervention based on common-path optical coherence tomography," IEEE Trans. on Biomed. Eng. 56(9),2318-2321(2009).
26. K. Zhang and J. U. Kang, "Common-path low-coherence interferometry fiber-optic sensor guided micro-incision," J. Biomed. Opt. 16(9),095003(2011).
27. R. Leitgeb, W. Drexler, A. Unterhuber, B. Hermann, T. Bajraszewski, T. Le, A. Stingl and A. Fercher, "Ultrahigh resolution Fourier domain optical coherence tomography," Opt. Express 12(10), 2156-2165(2004).
28. J. Y. Ha, M. Shishkov, M. Colice, W. Y. Oh, H. Yoo, L. Liu, G. J. Tearney, and B. E. Bouma, "Compensation of motion artifacts in catheter-based optical frequency domain imaging," Opt. Express 18(11), 11418-11427 (2010).
29. J. Lee, V. Srinivasan, H. Radharishnan, and D. A. Boas, "Motion correction for phase-resolved dynamic optical coherence tomography imaging of rodent cerebral cortex," Biomed. Opt. Express 19(22), 21258-21270 (2012).
30. D. D. Duncan and S. J. Kirkpatrick, "Processing algorithms for tracking speckle shifts in optical elastography of biological tissues," J. Biomed. Opt. 6(4), 418-426 (2001).
31. C. Song, P. L. Gehlbach, and J. U. Kang, "Active tremor cancellation by a "Smart" handheld vitreoretinal microsurgical tool using swept source optical coherence tomography," Opt. Express 20, 23414-23421 (2012)

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A distortion-corrected optical coherence tomography system, comprising:
an optical coherence tomography sensor;
a light source;
a fiber-optic system optically coupled to said light source and said optical coherence tomography sensor, said fiber-optic system arranged to provide a reference beam and an observation beam;
an optical detection system arranged to receive combined light from said reference beam and said observation beam, said optical detection system providing detection signals; and
a data processing system arranged to communicate with said optical detection system to receive said detection signals, construct a plurality of A-scans from said detection signals, and construct one or more images from said plurality of A-scans;
wherein, for at least one A-scan of said plurality of A-scans, said data processing system is configured to calculate a Doppler phase shift of said at least one A-scan caused by net axial motion of at least one of said optical coherence tomography sensor or a target of said optical coherence tomography sensor during free-hand scanning, estimate said net axial motion using said calculated Doppler phase shift, and correct distortion in said one or more images caused by said net axial motion by shifting said at least one A-scan according to said estimate.

2. The distortion-corrected optical coherence tomography system according to claim 1, wherein said data processing system is further configured to estimate said net axial motion using said calculated Doppler phase shift by calculating a global Doppler phase shift $\Delta\phi$ of said at least one A-scan by comparing said at least one A-scan to a previous A-scan.

3. The distortion-corrected optical coherence tomography system according to claim 2, wherein calculating a global Doppler phase shift $\Delta\phi$ further comprises averaging the phase shift of the pixels of said at least one A-scan according to the formula $$\Delta\varphi = \int \tan^{-1}\left[\frac{\operatorname{Im}[\tilde{I}_n(z) \bullet I_{n-1}^*(z)]}{\operatorname{Re}[\tilde{I}_n(z) \bullet I_{n-1}^*(z)]}\right] dz$$

where $\tilde{I}_n$ is the complex intensity of a pixel of said at least one A-scan at a particular axial position z, and $$[I_{n-1}]I_{n-1}^*$$

is the complex conjugate of the complex intensity of a pixel of said previous A-scan at a particular axial position z, where the tilde indicates a complex number and the asterisk indicates a complex conjugate.

4. The distortion-corrected optical coherence tomography system according to claim 1, wherein said data processing system is further configured to estimate said net axial motion using said calculated Doppler phase shift by calculating a speed of axial motion v(t) of said optical coherence tomography sensor using a global Doppler phase shift Δϕ calculated between said at least one A-scan and a previous A-scan.

5. The distortion-corrected optical coherence tomography system according to claim 4, wherein said speed of axial motion v(t) of said optical coherence tomography sensor is calculated according to the formula $$v(t) = \frac{\lambda_0}{\Delta t}\left(\frac{\Delta \varphi}{4\pi}\right)$$

where $\lambda_0$ indicates the central wavelength of a light source used in optical coherence tomography and Δt indicates a time interval between said at least one A-scan and said previous A-scan.

6. The distortion-corrected optical coherence tomography system according to claim 1, wherein said data processing system is further configured to estimate said net axial motion using said calculated Doppler phase shift by calculating an axial displacement d(t) of said optical coherence tomography sensor using a speed of axial motion v(t) of said optical coherence tomography sensor, which is calculated using a plurality of global Doppler phase shifts Δϕ corresponding to a plurality of A-scans received from said optical coherence tomography sensor.

7. The distortion-corrected optical coherence tomography system according to claim 6, wherein said estimate of said net axial motion is calculated according to the formula $$d(t) = \int_0^t v(t')dt'$$

where v(t) indicates the speed of axial motion of said optical coherence tomography sensor, which is calculated using a plurality of global Doppler phase shifts Δϕ corresponding to a plurality of A-scans received from said optical coherence tomography sensor.

* * * * *